(12) United States Patent
Ehninger et al.

(10) Patent No.: US 10,478,250 B2
(45) Date of Patent: Nov. 19, 2019

(54) ELECTROSURGICAL RETURN ELECTRODE AND RFID SYSTEM

(71) Applicant: Megadyne Medical Products, Inc., Draper, UT (US)

(72) Inventors: Michael D. Ehninger, South Jordan, UT (US); Paul R. Borgmeier, Salt Lake City, UT (US); Darcy W. Greep, Herriman, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 0 days.

(21) Appl. No.: 15/599,276

(22) Filed: May 18, 2017

(65) Prior Publication Data

US 2017/0360505 A1 Dec. 21, 2017

Related U.S. Application Data

(60) Provisional application No. 62/351,813, filed on Jun. 17, 2016.

(51) Int. Cl.

| A61B 18/16 | (2006.01) |
|---|---|
| A61N 1/04 | (2006.01) |
| G06K 7/08 | (2006.01) |
| H01Q 1/22 | (2006.01) |
| H01Q 7/00 | (2006.01) |

(Continued)

(52) U.S. Cl.
CPC .............. *A61B 18/16* (2013.01); *A61N 1/04* (2013.01); *G06K 7/086* (2013.01); *H01Q 1/2216* (2013.01); *H01Q 7/00* (2013.01); *H01Q 21/061* (2013.01); *A61B 18/14* (2013.01); *A61B 2018/165* (2013.01); *A61B 2018/167* (2013.01); *A61B 2034/2051* (2016.02); *A61B 2505/05* (2013.01); *A61B 2562/0223* (2013.01); *A61B 2562/08* (2013.01); *G06K 7/10* (2013.01);

(Continued)

(58) Field of Classification Search
CPC .... A61B 18/16; A61B 2562/0223; A61N 1/04
See application file for complete search history.

(56) References Cited

U.S. PATENT DOCUMENTS

| 4,736,752 A * | 4/1988 | Munck ................. A61N 1/0452 607/149 |
|---|---|---|
| 5,114,424 A * | 5/1992 | Hagen .................... A61B 18/16 606/32 |

(Continued)

*Primary Examiner* — William J Levicky
(74) *Attorney, Agent, or Firm* — Workman Nydegger

(57) ABSTRACT

An electrosurgical return electrode configured for operable association with a transponder detection unit. The return electrode includes a conductive element having an aperture array configured to allow passage of a magnetic, electric, or electromagnetic interrogation signal from the transponder detection unit through the conductive element and through the return electrode. The return electrode is positionable over a transponder detection unit such that the return electrode may be placed upon the transponder detection unit and a patient may be positioned upon the return electrode. The return electrode enables the detection of a transponder located on, within, and/or near the patient without the need for repositioning the patient relative to the return electrode and without the need for positioning an ancillary transponder reader or transmitter above the patient.

32 Claims, 10 Drawing Sheets

(51) Int. Cl.
*H01Q 21/06* (2006.01)
*A61B 18/14* (2006.01)
*G06K 7/10* (2006.01)
*A61B 34/20* (2016.01)

(52) U.S. Cl.
CPC ......... *G06K 7/1098* (2013.01); *G06K 7/1099* (2013.01); *G06K 7/10544* (2013.01)

(56) References Cited

U.S. PATENT DOCUMENTS

| | | | | |
|---|---|---|---|---|
| 6,544,258 | B2* | 4/2003 | Fleenor | A61B 18/16 128/908 |
| 7,107,097 | B2* | 9/2006 | Stern | A61N 1/0529 600/378 |
| 2005/0113817 | A1* | 5/2005 | Isaacson | A61B 18/16 606/32 |
| 2008/0237341 | A1* | 10/2008 | Fleck | G06K 7/10366 235/385 |
| 2014/0176390 | A1* | 6/2014 | Ko | H01Q 1/273 343/904 |

* cited by examiner

ELECTROSURGICAL RETURN ELECTRODE AND RFID SYSTEM

This application claims priority to and the benefit of U.S. Provisional Patent Application No. 62/351,813, filed Jun. 17, 2016, and entitled ELECTROSURGICAL RETURN ELECTRODE AND RFID SYSTEM, the entirety of which in incorporated herein.

BACKGROUND

1. Technical Field

The present disclosure relates generally to systems. In particular, the present disclosure relates to electrosurgical return electrodes configured for operative association with transponder identification systems, including radio frequency identification systems.

2. The Relevant Technology

During a medical procedure, it is often necessary to determine the presence of an object within a patient's body prior to completion of the procedure and closing of the patient. For instance, it is important to ensure that medical instruments, linens, sponges, gauze, pads, and other foreign materials are removed from a surgical site before a medical procedure is completed and the surgical site is closed. Failure to locate an object before finishing a procedure and closing a surgical site can lead to serious adverse medical effects. For example, if a foreign object is left within a patient, a resulting infection may necessitate additional surgery and treatment, and may even lead to patient death.

In order to track the use and return of objects used during a surgical procedure, some hospitals use procedures involving checklists or manually counting of objects used during the surgery. However, this type of approach is inefficient and prone to human error. Accordingly, another method involves the use of transponders and an associated wireless detection system. Typically, objects that are to be used in a procedure are each "tagged" with a transponder, and before the surgical procedure is finished, a surgeon or other personnel uses a transmitter to detect the presence of any tagged objects within the patient. Typically, a transmitter emits wireless signals in the radio or microwave frequencies to trigger a response from any transponders within range of the transmitter. A detector then detects any wireless signals returned by the transponders.

Transponders are typically configured as radio frequency identification (RFID) transponders, which are also commonly referred to simply as "tags." Some tags are active transponders, having an onboard power source such as a battery, and other tags are passive transponders, deriving power for generating a return signal from the interrogation signal transmitted by an RFID reader.

In some instances, a wireless transponder detection system includes a mat having one or more antennae for automatically transmitting interrogation signals to an area near the mat, such that a patient positioned on the mat is within the range of the transmitted interrogation signals. Such mat-based systems are often favored for their ability to simplify the transponder detection process, provide a wide scan of the patient, and reduce surgery time.

In the area of electrosurgery, medical procedures of cutting tissue and/or cauterizing leaking blood vessels are performed by utilizing radio frequency (RF) electrical energy. As is known to those skilled in the medical arts, electrosurgery is widely used and offers many advantages including that of the use of a single surgical tool for both cutting and coagulation. The RF energy is produced by a wave generator or Electro-Surgical Unit (ESU) and transmitted to a patient's tissue through a hand-held electrode that is operated by a surgeon.

Monopolar electrosurgical generator systems have an active electrode that is applied by the surgeon to the patient at the surgical site to perform surgery and a return electrode that acts as the path from the patient back to the ESU. The active electrode at the point of contact with the patient must be small in size to produce a high current density in order to produce a surgical effect of cutting or coagulating tissue. The return electrode, which carries the same RF signal as the active electrode, must be large enough in effective surface area at the point of communication with the patient such that a low density current flows from the patient to the return electrode.

While advances in the fields of transponder detection systems and electrosurgical return electrodes have been beneficial, there remains room for improvement. In particular, the accuracy and functionality of transponder detection systems during an electrosurgical procedure where a return electrode, and more specifically a large capacitive pad type return electrode, is in use remains an issue. More particularly, an electrosurgical return electrode will often interfere with the interrogation signal and/or return signal of a transponder detection system, and especially mat-based transponder detection systems, which can lead to inoperability or reduced operability of the transponder detection system.

Therefore, it would be an advance in the present fields to provide an electrosurgical return electrode that is configured for functional and accurate use with an integrated or separate transponder detection system.

BRIEF SUMMARY

The present disclosure addresses at least some of the foregoing shortcomings by disclosing a return electrode configured to enable sufficient passage of a magnetic, electric, or electromagnetic interrogation signal from an associated transponder detection unit (e.g., an RFID transponder transmitter/reader) while maintaining sufficient electrosurgical return electrode functionality.

Typically, in an electrosurgical procedure where transponder detection is desired, a return electrode will be positioned on top of a transponder detection unit (e.g., mat or pad), both of which are positioned upon a table, chair, or other patient support structure. A patient may then be positioned upon the return electrode while the electrosurgical procedure is carried out. Beneficially, because one or more features and/or components of the return electrodes of the present disclosure are configured to enable an interrogation signal to pass from the transponder detection unit through the return electrode and to an area in which the patient or targeted portion of the patient resides, detection of transponder tagged objects located on, within, and/or near the patient is enabled without requiring removal of the return electrode or adjustment/movement of the patient and without the need for positioning an ancillary transponder reader or transmitter above the patient or performing additional transponder detection steps.

In some embodiments, a return electrode is configured as a stand-alone or separate unit that may be used with a stand-alone or separate transponder detection unit during an electrosurgical procedure. For example, some embodiments of return electrodes are able to be positioned upon a separate transponder detection unit. A patient may then be appropriately positioned upon the return electrode, and an electrosurgical procedure may be performed while both the return electrode and the transponder detection unit are utilized. Alternatively, some embodiments include an integrated return electrode and transponder detection unit (e.g., formed as a "one-piece" mat, pad, or other structure) configured to provide return electrode functionality while also enabling transponder detection functionality.

In some embodiments an electrosurgical return electrode includes a conductive element configured to conduct electrical current. The conductive element has opposing first and second major surfaces and includes an aperture array configured to allow passage of a magnetic, electric, or electromagnetic interrogation signal from an associated transponder detection unit through the conductive element. The return electrode also includes a patient contact pad positioned adjacent the first major surface of the conductive element and configured to be disposed between the conductive element and a patient when the patient is at least partially positioned upon the patient contact pad. The electrosurgical return electrode is configured to be at least partly positionable upon a transponder detection unit with the second major surface facing the transponder detection unit.

In some embodiments, an electrosurgical return electrode and transponder detection system includes a transponder detection unit and a return electrode unit positioned above the transponder detection unit. The transponder detection unit and return electrode unit are operably associated to enable the transponder detection unit to detect a transponder located in a target area above the return electrode unit and within range of the transponder detection unit.

In some embodiments, a method for detecting a transponder in an electrosurgical environment includes positioning a patient at least partially upon an electrosurgical return electrode and transponder detection system. The method can also include actuating the transponder detection unit to send a magnetic, electric, or electromagnetic interrogation signal to a target area that includes or is near at least a portion of the patient and receiving a return signal from the transponder indicating presence of the transponder at the target area.

BRIEF DESCRIPTION OF THE DRAWINGS

To further clarify the above and other advantages and features of the present disclosure, a more particular description will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which.

DETAILED DESCRIPTION

The electrosurgical return electrodes disclosed herein are configured for operable association with a transponder detection unit, such as an RFID transponder detection unit. As described herein, one or more components or features of the return electrodes enable effective use of the return electrodes for electrosurgical purposes while also enabling passage of a magnetic, electric, or electromagnetic interrogation signal from the associated transponder detection unit through one side of the return electrode to a target area on the opposite side of the return electrode. In some embodiments, a transponder detection unit will be in the form of a mat or pad positioned upon a table, chair, or other patient support structure, and the return electrode is positioned on top of the transponder detection unit before a patient is positioned upon the return electrode. In other embodiments, the return electrode and transponder detection unit are integrated into a single unit. In either case, the return electrode enables the detection of a transponder located on, within, and/or near the patient without the need for repositioning the patient relative to the return electrode and without the need for positioning an ancillary transponder reader or transmitter above the patient.

Transponder Detection Units

Figure 1:
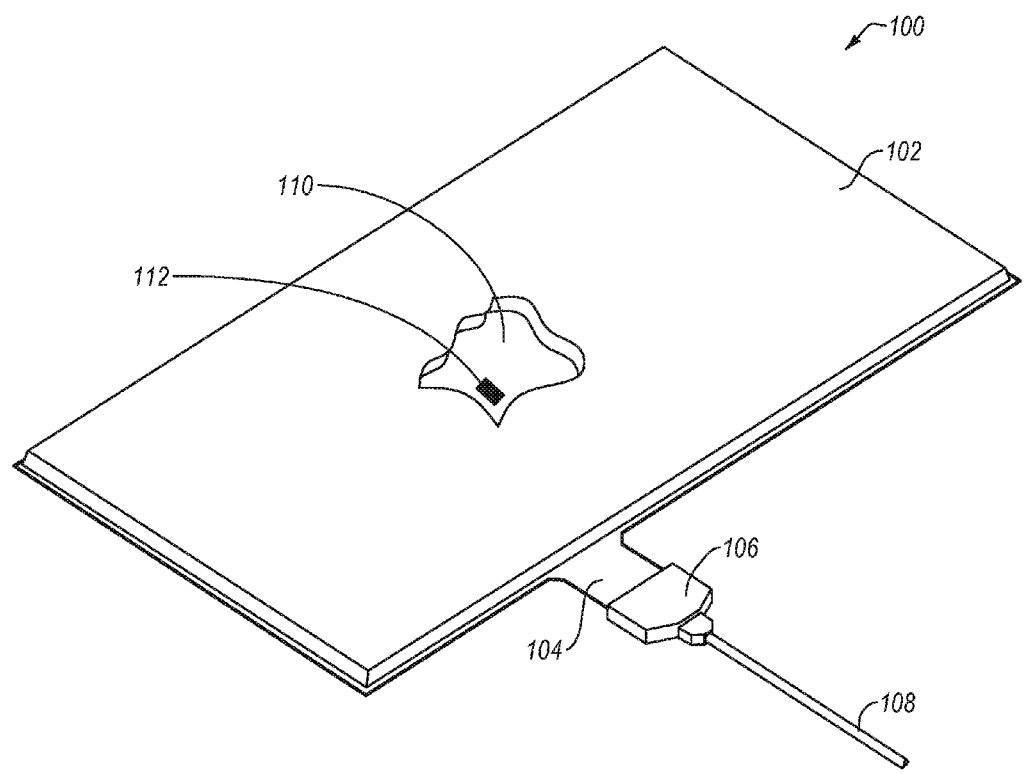
FIG. 1 illustrates a transponder detection unit usable with one or more return electrodes of the present disclosure.

FIG. 1 illustrates an embodiment of a mat-based transponder detection unit 100 suitable for use with one or more of the electrosurgical return electrodes disclosed herein. The illustrated mat-based transponder detection unit 100 includes a mat 102, a tab 104 extending from the mat 102 for coupling to a cable interface 106 of a power cable 108. The power cable 108 is configured to deliver electrical current to one or more antennas, discussed in more detail below, disposed within the mat 102.

The mat 102 is configured to be positionable on a patient support structure such as a bed, surgical table, chair, or other structure that functions to support a patient or a portion of a patient during a medical procedure. In some embodiments, the mat 102 is removably attachable to a patient support structure. For example, the mat 102 may include one or more ties, clamps, hook and loop fasteners, bands, and/or other fastening means for removably securing the mat 102 to a support structure.

The transponder detection unit 100 is operable to ascertain a presence or absence of an object 110 (e.g., a surgical linen or rag, as shown) tagged with one or more transponders 112 which may be in or on a patient positioned on the mat 102 or otherwise within an interrogation field of the detection unit 100. For example, receipt of a response signal to an interrogation signal may indicate a presence of the transponder 112 in a target area or field of interrogation of the detection unit 100. In some embodiments, interrogated transponders are passive, and the associated response signal(s) does not include additional information. Additionally, or alternatively, detection unit 100 may be operable to read information encoded or stored in one or more transponders, write information to a memory in one or more transponders, and/or send instructions or commands to one or more transponders for the transponders to execute.

Objects that may be tagged with transponders configured to respond to an interrogation signal sent from the mat 102 of the detection unit 100 include medical instruments (e.g., electrosurgical components, clamps, hemostats, scalpels), linens, sponges, gauze, bandages, padding, and/or other objects used during a medical procedure.

In some embodiments, one or more transponders are radio frequency identification (RFID) transponders, preferably passive transponders. One or more RFID transponders may be configured to store a unique identifier, to allow information to be read from the RFID transponder, and/or to store information wirelessly sent to the RFID transponder to execute various commands. In some embodiments, RFID transponders are configured to simply emit a response signal upon receipt of an interrogation signal.

Figure 2:
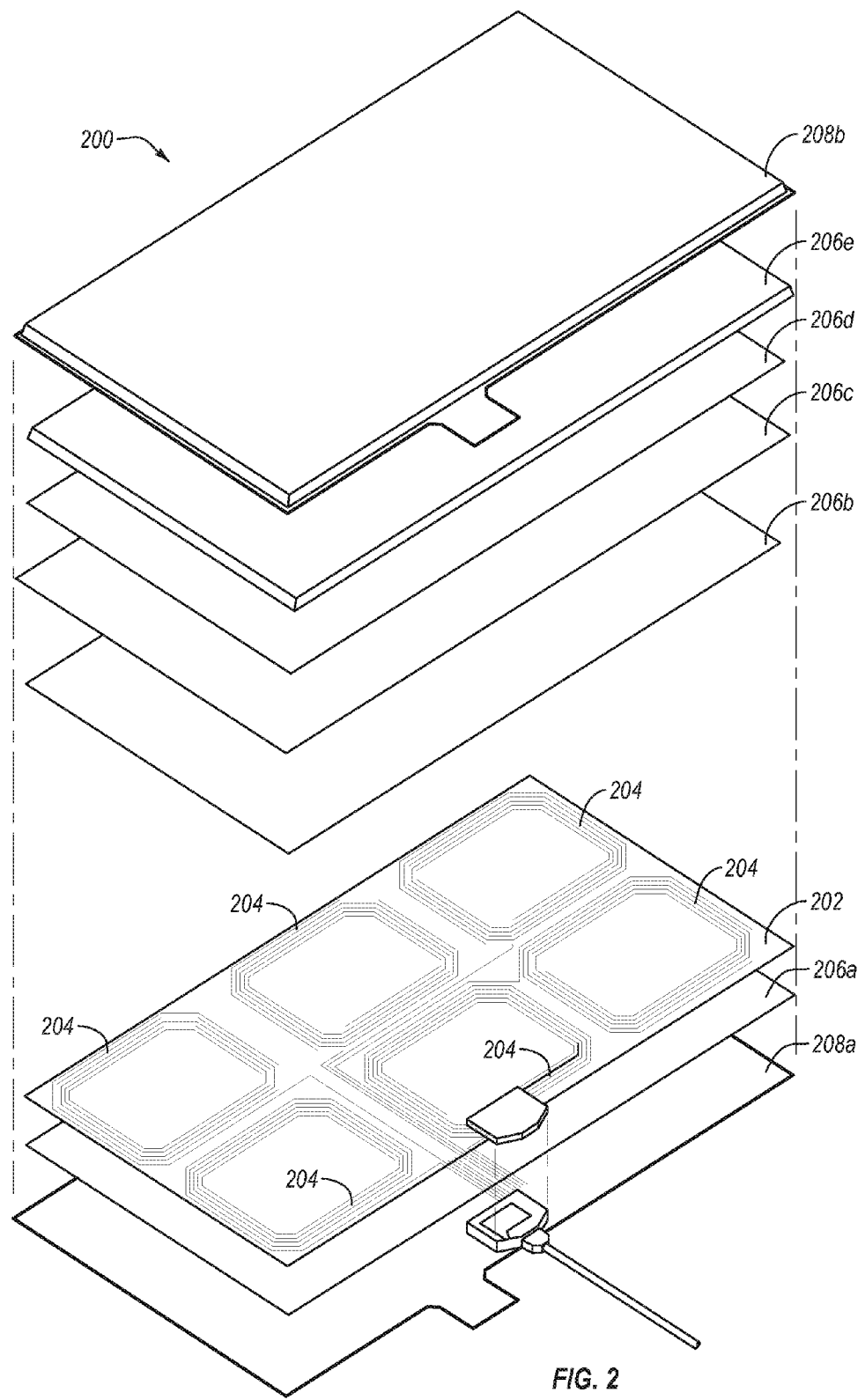
FIG. 2 illustrates an exploded view of an embodiment of a transponder detection unit usable with one or more return electrodes of the present disclosure.

FIG. 2 illustrates an exploded view of an embodiment of a mat-based transponder detection unit 200. As shown, the illustrated embodiment includes a base layer 202 formed from an electrically insulative material. The base layer 202 may, for example, take the form of a polyethylene film and/or may take the form of a laminate structure comprised of multiple plies of material.

The illustrated detection unit 200 also includes antennas 204. In this embodiment, the antennas 204 are formed as one or more traces of an electrically conductive material (e.g., metals, graphite, graphene) supported and/or joined to the base layer 202 (e.g., on one or both surfaces of the base layer 202 and/or in between laminate layers of the base layer 202). The conductive traces may be formed by silk-screen printing, photo-etching, or by other printing or deposition (e.g., chemical vapor deposition) techniques commonly used in the electronics industry.

Antennas 204 may be positioned as an arrangement of one or more linear antenna arrays of coil antennas (or alternatively, slot or dipole antennas, for example), as shown. Other arrangements may also be used (e.g., staggered arrangements, arrangements without linear or two-dimensional arrays, overlying antennas). In some embodiments, the antenna array is configured to provide substantially complete coverage over the body of a patient or the targeted portion of a patient (e.g., the portion surrounding and including a surgical site). Other embodiments may include a greater or fewer number of antenna coils than illustrated.

The illustrated embodiment also includes a number of intermediate layers 206a-206e configured to protect the antennas 204, to provide pressure relief to a patient supported by the device, to provide thermal insulation, and/or to make sterilization easier. For example, intermediate layer 206a and intermediate layer 206b (positioned on opposite sides of the base layer 202), may be configured to protect the antennas 204 from bending too sharply, de-laminating, splitting, etc.; intermediate layer 206c may be formed as a thermoplastic (e.g., thermoplastic polyurethane) configured to enhance the ability to sterilize the detection unit 200 using conventional sterilization techniques; intermediate layer 206d may be formed as a gel layer configured to provide patient pressure relief and/or thermal insulation; and intermediate layer 206e may be formed as a foam layer configured to provide patient pressure relief and/or thermal insulation (e.g., in addition to a gel layer).

In some embodiments, the intermediate layers 206a and 206b are formed of silicon with sufficient stiffness to provide a desired level of protection. In some embodiments, intermediate layers 206a and 206b are about 0.10 to 0.15 inches thick, or about 0.125 inches thick. In some embodiments, a gel layer is about 0.2 to 0.3 inches thick, about 0.225 to 0.275 inches thick, or about 0.25 inches thick. In some embodiments, a foam layer is about 0.25 to 0.50 inches thick, or about 0.375 inches thick. In some embodiments, a thermoplastic layer is about 0.001 to 0.002 inches thick, or about 0.0015 inches thick.

The illustrated embodiment also includes covers 208a and 208b. In some embodiments, covers 208a and 208b are formed from a stretchable material (e.g., nylon polyurethane laminate) to provide a tight and smooth fit over the other layers of the detection unit 200. In some embodiments, the bottom cover 208a is formed from or is attached to a non-slip material. In some embodiments, the covers 208a and 208b are attached to each other (e.g., around the periphery) to enclose or partially enclose an interior of the detection unit 200.

Although the illustrated embodiment includes covers and a plurality of intermediate layers, other embodiments may omit one or more covers or intermediate layers, or may include a different configuration of covers and/or intermediate layers. For example, some transponder detection units may omit one or more of a foam layer, gel layer, thermoplastic layer, and/or protective layer. As described in more detail below, some embodiments of transponder detection units are configured to be operatively associated with an electrosurgical return electrode as part of an integrated transponder detection return electrode system (e.g., as opposed to other embodiments where an electrosurgical return electrode is placed upon a separate transponder detection unit). Such embodiments, for example, may omit one or more intermediate layers and will typically omit a top cover to enable electrosurgical return electrode components to be positioned directly adjacent to other layers of the transponder detection unit.

Mat-based transponder detection systems suitable for use with one or more of the electrosurgical return electrodes described herein are also described in U.S. Pat. Nos. 9,136, 597, and 8,264,342, the disclosures of which are incorporated herein in their entirety.

Electrosurgical Return Electrodes

Electrosurgical return electrodes described herein are configured to be operable with one or more transponder detection units, such as a transponder detection unit described in connection with FIGS. 1 and 2. In some embodiments, a return electrode is configured as a stand-alone or separate unit that may be used with a stand-alone or separate transponder detection unit during an electrosurgical procedure. For example, some embodiments of return electrodes are able to be positioned upon a separate transponder detection unit. A patient may then be appropriately positioned upon the return electrode, and an electrosurgical procedure may be performed while both the return electrode and the transponder detection unit are utilized. Alternatively, some embodiments include an integrated return electrode and transponder detection unit (e.g., formed as a "one-piece" mat) configured to provide return electrode functionality while also enabling transponder detection functionality. As described in further detail below, return electrode components (either as part of a stand-alone return electrode or as part of an integrated return electrode and transponder detection unit) of the present disclosure are configured to enable accurate and effective transponder detection while also providing efficient return electrode functionality.

In some embodiments, a return electrode is a self-limiting return electrode that: (1) can maintain the return current density on the surface of the patient at sufficiently low levels; (2) can maintain the electrical impedance between the electrode and the patient at sufficiently low levels so that electrical energy is not concentrated sufficiently to heat the skin of the patient at any location in the electrical return path by more than six degrees (6°) Celsius; and (3) has characteristics of materials and geometries that are such that if the effective surface area is reduced below a selected threshold level, there will be insufficient energy dissipated at the surgeon's implement for him to continue effectively using the implement in its electrosurgical mode. Return electrode configurations that demonstrate such functionality are taught by U.S. patent application Ser. No. 14/583,315, published as U.S. 2015/0182280, incorporated herein by reference in its entirety.

Return electrodes of the present disclosure may be configured to be coupled to a conventional radio frequency electrical power generator, such as but not limited to constant power, voltage, and/or current or variable power, voltage and/or current generators. Conventional electrical conductors typically connect the generator to the surgeon's implement and the electrosurgical return electrode.

Figure 3:
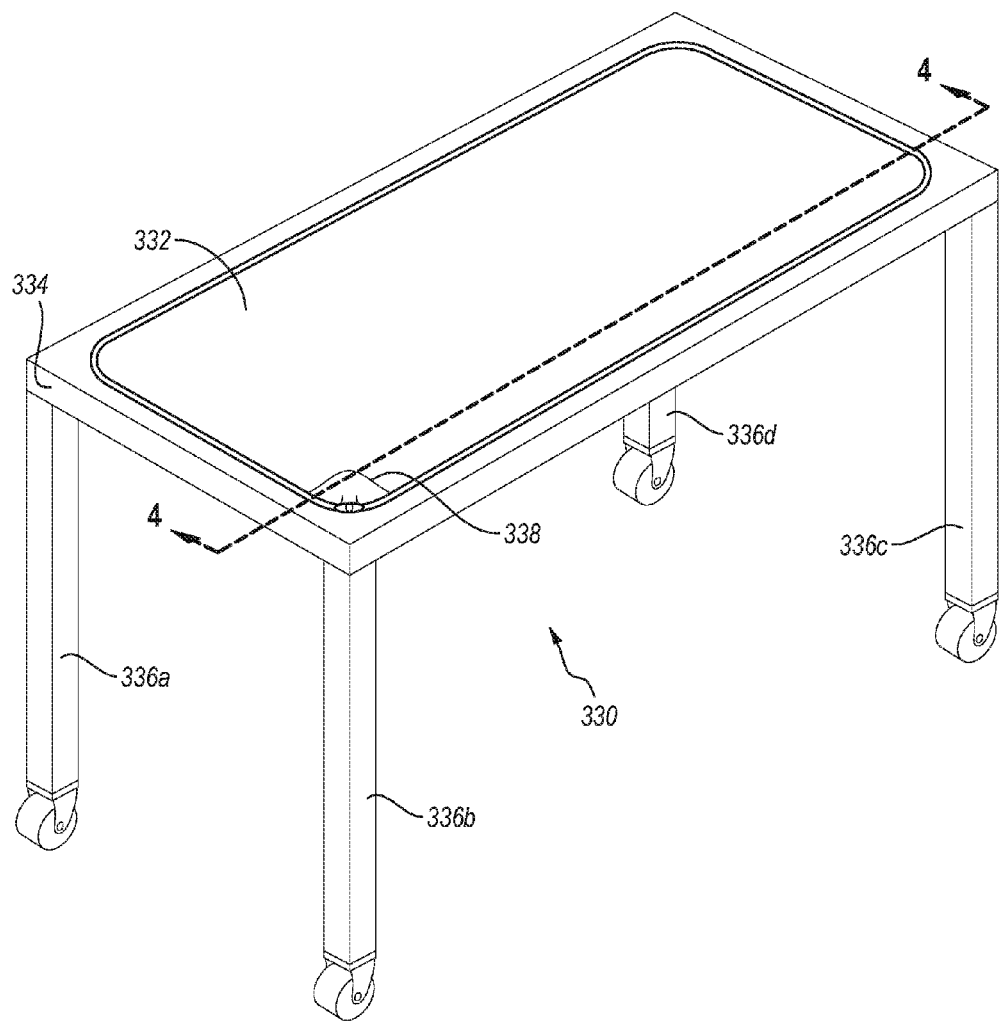
FIG. 3 illustrates an embodiment of an electrosurgical return electrode.
Figure 4:
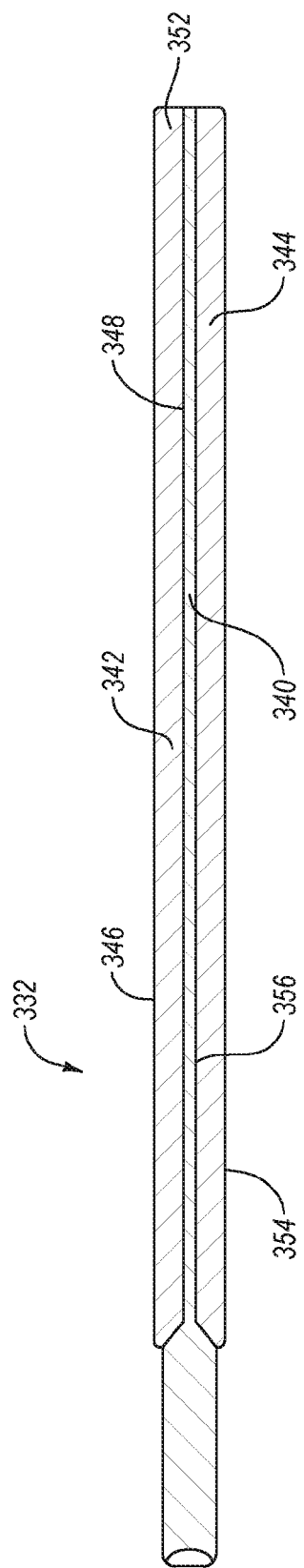
FIG. 4 illustrates a cross-sectional view of the electrosurgical return electrode of FIG. 3.

Reference is now made to FIGS. 3 and 4, which illustrate an electrosurgical return electrode 332 according to one example embodiment of the present disclosure. Return electrodes, such as the embodiment shown, are typically electrically connected to an electrical power generator, which is also electrically connected to the surgeon's implement. In FIG. 3, electrosurgical return electrode 332 is shown in perspective on operating table 330 with electrosurgical return electrode 332 according to the present disclosure disposed on the upper surface thereof, an edge of table 330 being identified by reference number 334. Operating table 330 is shown to have conventional legs 336a-336d that may be fitted with wheels or rollers as shown. Table 330 is one structure that is capable of performing the function of supporting means for supporting a patient during treatment. It may be appreciated by one skilled in the art, however, that various other configurations of support means are possible and capable of performing the required function. For example, supporting means may include but not be limited to chairs, plates, beds, carts, and the like.

Return electrode 332, as illustrated in FIGS. 3 and 4, may be made of conductive plastic, rubber, or other flexible material. Silicone, butyl rubber, or urethane have been found to be particularly attractive materials as they are flexible, as well as readily washable and sterilizable. Alternatively, the main body of the return electrode may be made of inherently relatively high resistance flexible material altered to provide the requisite conductivity. A preferred example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors.

Further reference to FIG. 3 reveals the presence of a conventional electrical connector 338 attached to return electrode 332 to provide a conventional electrical return to the electrosurgical radio frequency energy source (not shown). Connector 338 is another structure capable of performing the function of connecting means for making electrical connection to the return electrode. Connector 338 is only illustrative of one possible structure for performing the desired function; it being appreciated by one skilled in the art that various other structures are capable of performing the required function.

Although, in FIG. 3, the entire upper surface of table 330 is shown as being covered with return electrode 332, it should be understood that entire coverage is by no means required in order to practice the principles of the disclosure. Thus, when used with conventional electrosurgical generators, the return electrode needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage.

It has been found that at conventional electrosurgical frequencies, this has necessitated only an effective working surface area no larger than about the projected outline of one-third of the torso for an adult patient lying on an operating table or a portion of the buttocks of a patient sitting in a chair. However, the effective working surface area will vary depending on the material used, in some geometrical configurations, and in instances where various layers of operating room linens are placed over the electrode. The principles hereof may be successfully employed and the effective working surface area of the return electrode determined in such circumstances by routine experimentation. Under certain conditions, the effective working surface may be as small as about seven square inches (or about 45 square centimeters).

Moreover, although return electrode 332 shown in FIG. 3 is depicted as being rectangular in shape, it will be evident that return electrodes according to the present disclosure could be oval or contoured as, for example, to follow the silhouette of the at least a portion of the torso or other principal part of the body of a patient.

Those skilled in the art know that, with the currently used disposable return electrodes, reducing the effective size of the electrode to about three square inches will not reduce the RF current flow to a level where it will impede the surgeon's ability to perform surgery nor concentrate current to a level to cause patient trauma. However, to provide for some spacing of the electrode from patient's body, a return electrode according to the present disclosure, may need a minimum effective surface area of between about 7 and about 11 square inches (about 45 $cm^2$ to about 70 $cm^2$) with a relatively small separation from the skin of the patient such as that provided by a surgical gown or no interposing gown at all. Such an effective surface area is easy to obtain if the patient is positioned on an electrode that is the size of at least a portion of their upper torso or larger.

It will be observed that when return electrode 332 is laid out on operating table 330, the upper exposed, or working, surface of the electrode again is expansive so as to enable low return current density. Although it is not necessary that the electrode cover the entire surface of an operating table or the entire seat surface of a medical, dental or other patient chair, it has been found advantageous in some instances to provide a greater surface area than that of the projected area of a portion of the buttocks or torso of a patient so that if a patient position shifts during the course of a procedure, a sufficient portion of the patient will remain in registration with the electrode surface so that the effective impedance will remain within desirable ranges.

In some embodiments, therefore, the electrode does not need to be in direct contact with a patient, either directly or through intervening conductive or nonconductive gel. In addition, because of the expansive size of the electrode, there is no need for tailoring the electrode to fit physical contours of a patient. While it has been found that with selected materials and geometries, the preferred self-correcting and self-limiting properties could be achieved in an electrode as small as about seven square inches (or about 45 square centimeters) in working surface area, the preferable range of exposed upper working surface area of the electrode lies in the range of from about 11 to 1,500 square inches (or about 70 to 9,680 square centimeters). By making the electrode several times larger (typically, at least an order of magnitude larger) in working surface area than steel plates or sticky pads, the need for direct physical attachment, either directly to the skin of the patient or through gels, is eliminated.

Attention is now directed to FIG. 4, which illustrates a simplified section taken along the lines 4-4 of FIG. 3. As illustrated in FIG. 4, return electrode 332 includes a conductive element 340 and pads 342, 344 on opposing sides of conductive element 340. Conductive element 340, in one configuration, is made of a conductive plastic, rubber, fabric or other flexible material which, when employed as a conductive element, will result in an effective DC resistance that will maintain current densities below levels that could result in injuries to patients. Various materials may be appropriate to give the required impedance. For example, silicone, butyl rubber, or urethane have been found to be particularly attractive materials for conductive element 340 as they are flexible, as well as readily washable, disinfectable, and sterilizable. Alternatively, in another embodiment, conductive element 340 may be made of an inherently relatively high resistance flexible material altered to provide the requisite conductivity. One example of the latter is that of silicone rubber material in which there are impregnated conductive fibers, such as carbon black, quantities of gold, silver, nickel, copper, steel, iron, stainless steel, brass, aluminum, or other conductors.

In some embodiments, conductive element 340 is fabricated from a material and/or is configured in size and shape so that it is substantially transparent to one or more wavelengths of electromagnetic radiation, such as but not limited to, microwave radiation, infra-red (IR) radiation, ultraviolet (UV) radiation, X-ray radiation, radio frequency (RF), and the like. This allows conductive element 340 and return electrode 332, when the other components of return electrode 332 are transparent to one or more wavelengths of electromagnetic radiation, to be maintained in place during performance of certain medical procedures using particular wavelengths of electromagnetic radiation. As described below, conductive elements may be configured to allow sufficient passage of magnetic fields, generated by an associated transponder detection unit, through the conductive element and through the return electrode.

It may be appreciated by one skilled in the art that conductive element 340 may have various other configurations so long as conductive element 340 is capable of performing the functions of an electrode, i.e., being capable of passing current therethrough. For example, in some embodiments, conductive element 340 includes a thin, highly conductive lower stratum that facilitates connection of return electrode 332 to an electrosurgical radio frequency energy source (not shown). In another alternate embodiment, conductive element 340 is configured from multiple layers of conductors. In still yet another embodiment, conductive element 340 includes an outer dielectric layer that substantially surrounds an interior-conducting layer, similar to the self-limiting electrosurgical electrodes described previously.

Referring again to FIG. 4, disposed on opposing sides of conductive element 340 are pads 342, 344. As can be seen, pad 342 has an outer surface 346 and an inner surface 348. Outer surface 346 is configured to be placed against the surface of a patient (thereby acting as a working surface of return electrode 332), while inner surface 348 is disposed next to conductive element 340. In some embodiments, inner surface 348 is secured to conductive element 340, such as with an adhesive, to prevent air bubbles or separation between pad 342 and conductive element 340. Pad 342 may include outer and inner cover layers that are formed individually and secured together about their edges or are integrally formed. The outer and inner cover layers may define outer and inner surfaces 346, 348. Outer and inner cover layers may be formed of various materials, such as urethane, polyurethane, polyethylene, polypropylene, polyolefins, polyvinyl chloride, PET, etc. A fill material 352, discussed below, may be disposed between the outer and inner cover layers.

Similar to pad 342, pad 344 includes an outer surface 354 and an inner surface 356. Inner surface 356 is disposed next to conductive element 340. Outer surface 354 is configured to be placed on a support surface (e.g., operating table, chair, etc.), or to be placed on a transponder detection unit (such as a transponder detection unit described in FIGS. 1 and 2), or to be attached to other transponder detection components or layers as part of a one-piece system or mat. Like outer and inner cover layers 346, 348, one or both of outer surface 354 and inner surface 356 may be attached to, defined by, or bounded by a cover layer formed of various materials, such as urethane, polyurethane, polyethylene, polypropylene, polyolefins, polyvinyl chloride, PET, etc. Like pad 342, inner surface 356 may be secured to conductive element 340, such as with an adhesive, to prevent air bubbles or separation between pad 344 and conductive element 340. In other embodiments, however, the edges of pad 344 may be secured to the edges of pad 342 with conductive element 340 disposed therebetween. Also like pad 342, pad 344 may include a fill material.

Fill materials used in pads 342, 344 may provide return electrode 332 with some pressure reducing characteristics. More specifically, since pads 342, 344 retain a defined volume of fill material, when an individual rests upon return electrode 332, the fill materials distribute the downward force of the patient throughout the fill materials, thereby decreasing the point forces applied to those parts of the patient's anatomy where bony prominences are located. Nevertheless, as discussed elsewhere herein, pads 342, 344 are relatively thin to ensure sufficient coupling between a patient and conductive element 340. Accordingly, in some situations, such as during lengthy surgical procedures, it may be desirable or necessary to use a separate pressure reducing pad in combination with return electrode 332 to prevent the formation of pressure sores on the patient or to increase the patient's comfort level.

Fill materials used in pads 342, 344 may act as dielectric layers to prevent current flow through pads 342, 344, respectively. Alternatively, the fill materials may take the form of conducting materials to aid with the transmission of current therethrough. Additionally, the fill materials may provide a thermal mass for the distribution of heat during an electrosurgical procedure. The thermal mass provided by the fill materials assists with the distribution of heat throughout the patient's body and substantially eliminates, (e.g., in combination with self-limiting characteristics of return electrode 332), the potential for hot spots that may burn the patient. Consequently, the substances used for fill materials may perform multiple functions during an electrosurgical procedure.

In general, the fill materials may take the form of one or more solids, liquids, gases, or combinations thereof depending on the pressure reducing, dielectric, and/or conducting properties needed for return electrode 332. For example, in one illustrative embodiment, the fill materials are elastomeric gels having low durometer level, such as SORBOTHANE. In addition to SORBOTHANE, various other elastomeric gels may be used, such as but not limited to those based upon the polymer chemistry of urethanes, silicones, hydrophilic elastomers or hydrogels, vinyls, vinyl alcohols, or other similar materials and technologies. Additionally, the fill materials may take the form of water, saline, water based materials, conductive oils, and the like. Still further, the fill materials may take the form of solid but flexible foam-type materials.

In some embodiments, such as those in which the return electrode is integrated with transponder detection components or layers as a one-piece system or mat, the pad 344 may be formed as one or more of the intermediate layers 206b-206e discussed in relation to FIG. 2. In such embodiments, an interrogator or reader may be joined (e.g., adhered) to the pad 344 at the outer surface 354. For example, a base layer and one or more antennas (such as base layer 202 and antennas 204), and optionally other intermediate layers, may be adhered to or otherwise affixed against the outer surface 354. In some embodiments, one or more additional cover materials may then be used to enclose the integrated one-piece mat or system.

The materials forming return electrode 332, conductive element 340, and/or pads 342, 344, at least partially control the passage of current from a patient to conductive element 340. As such, in one embodiment, pads 342 and/or 344 are insulative. In an alternate configuration, pads 342 and/or 344 may be conductive and aid in the passage of current from the patient to conductive element 340. So long as the return electrode 332 provides the self-limiting characteristics described herein, the various elements of return electrode 332, i.e., conductive element 340 and/or pads 342, 344, may provide one or more resistive, inductive, and/or capacitive inductance components to the bulk impedance of the return electrode. In this manner return electrode 332 is self-limiting, while also providing at least some pressure reducing characteristics.

In addition to the materials used to form pads 342, 344, the thickness and arrangement of pads 342, 344 and conductive element 340 can affect the transmission of current from a patient to conductive element 340. By way of non-limiting example, the distance between outer surface 346 of pad 342 and conductive element 340 can affect the capacitive coupling between conductive element 340 and a patient resting upon the outer surface 346 of return electrode 332. Through this capacitive coupling, current used during electrosurgery is passed from the patient to return electrode 332. As will be understood by one of ordinary skill in the art in light of the disclosure herein, the capacitive coupling between the patient and return electrode 332 can be directly related to the self-limiting characteristics of return electrode 332. Thus, by changing the distance between the outer surface 346 and the conductive element 340, the capacitive coupling between the patient and the return electrode 332 can be adjusted.

In some embodiments, one or both of pads 342, 344 have an approximate thickness of between about 0.02 inches and about 0.120 inches. In other embodiments, one or both of pads 342, 344 have an approximate thickness of less than about 0.10 inches, about 0.09 inches, about 0.075 inches, about 0.06 inches, about 0.05 inches, about 0.03 inches, or about 0.02 inches. In some embodiments, return electrode 332 has a total thickness of about 0.135 inches or less. In some embodiments, limiting the thickness of pads 342, 344 to below about 0.120 inches, about 0.10 inches, about 0.09 inches, about 0.075 inches, about 0.06 inches, about 0.05 inches, about 0.03 inches, or about 0.02 inches can enable return electrode 180 to present a level of resistance that allows for uneven distribution of current being transferred from a patient to conductive element 340.

In addition or as an alternative to adjusting the thickness of pads 342, 344 (e.g., limiting the thickness to the dimensions identified herein), the dielectric constants of the materials used in pads 342, 344, or portions of the materials thereof, may be adjusted to achieve the desired level of capacitive coupling and/or resistance presented by return electrode 332. The materials used to form pads 342, 344 may be selected, at least in part, based upon the value of their dielectric constants. Similarly, the materials used in pads 342, 344, or portions thereof, may be altered (e.g., by doping) to adjust their dielectric constants in order to provide the desired capacitance and/or resistance.

Transponder Detection and Return Electrode Systems

As indicated above, embodiments of the present disclosure include one or more features and/or components configured to enable an electrosurgical return electrode to be used in conjunction with a transponder detection system without, for example, requiring a patient to be adjusted or moved during a procedure in order to ensure accurate transponder detection.

In an electrosurgical procedure where transponder detection is desired, a return electrode according to the present disclosure may be positioned on top of a transponder detection unit (e.g., mat or pad), both of which are positioned upon a table or other patient support structure. A patient may then be positioned upon the return electrode while the electrosurgical procedure is carried out. Beneficially, because one or more features and/or components of the return electrode are configured to enable an interrogation signal to pass from the transponder detection unit through the return electrode and to an area in which the patient or targeted portion of the patient resides, detection of transponder tagged objects is enabled without requiring removal of the return electrode or adjustment/movement of the patient.

Figure 5:
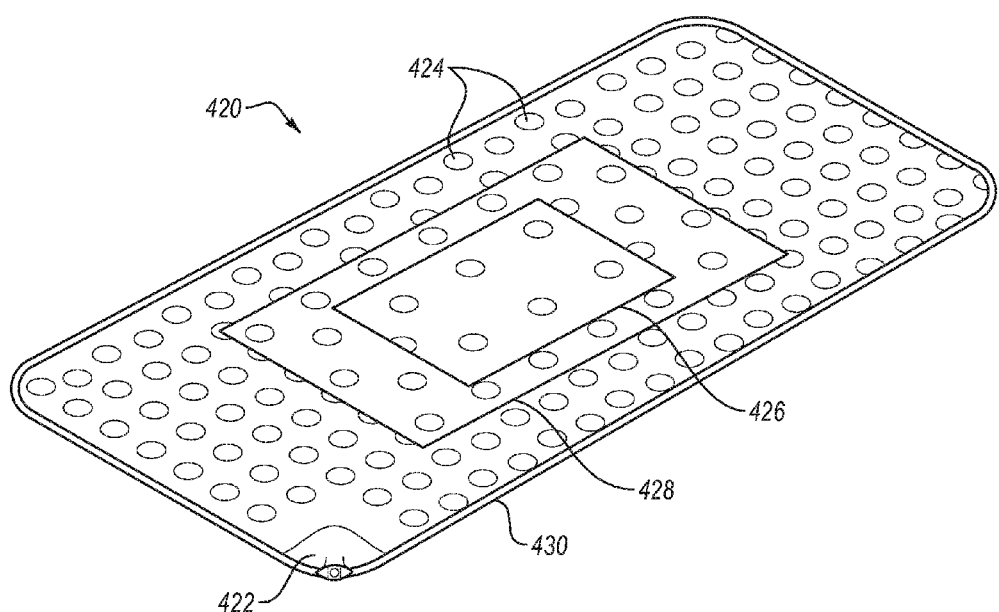
FIG. 5 illustrates an embodiment of an electrosurgical return electrode having a conductive element with an aperture array.

FIG. 5 illustrates a perspective view of a return electrode 420. Return electrode 420 may be similar or identical to the other embodiments described herein in some aspects. For instance, return electrode 420 includes a conductive element, a connector 422, and a pad disposed on each side of the conductive element Like return electrode 332, return electrode 420 may be reversible. That is, return electrode 420 may have two opposing major surface that can be alternately used as working surfaces during electrosurgical procedures, with the opposite surface being oriented toward the transponder detection unit.

In this embodiment, the conductive element defines a plurality of apertures or openings 424 extending therethrough. Embodiments of conductive elements having a plurality of apertures have beneficially shown the ability to allow sufficient transmission of an interrogation signal from one major surface of the return electrode to the other, enabling the use of an adjoined, integrally attached, or otherwise operably associated transponder detection system with the return electrode. For example, when a transponder detection unit, such as shown in FIGS. 1 and 2, is in operation, an interrogation signal is sent in the form of a magnetic, electric, or electromagnetic field generated by the passage of current through one or more antennas (e.g., coils). By appropriately configuring and positioning the apertures of the conductive element, a sufficient amount of the magnetic, electric, or electromagnetic field lines of the generated interrogation signal are passable through the return electrode so as to induce a response signal from any transponders located within the targeted area beyond the return electrode (e.g., where a patient may be positioned).

In the illustrated embodiment, the plurality of apertures 424 are arranged in three distribution areas. The first distribution area 426 is positioned near the center of return electrode 420. As can be seen, there are relatively few apertures within first distribution area 426 and they are spread apart from one another. The second distribution area 428 is disposed concentrically about first distribution area 426. Second distribution area 428 includes a higher density of apertures 424 than first distribution area 426. The third distribution area 430 is disposed concentrically about second distribution area 428 and includes a higher density of apertures 424 than first and second distribution areas 426, 428. In some other embodiments, apertures are spaced uniformly throughout the conductive element, without a substantial change in density from one portion of the return electrode to another. In still other embodiments, area 426 may have a higher density of apertures than area 428 and/or 430. Similarly, in some embodiments, area 428 may have a higher density of apertures than area 426 and/or 430.

Although apertures 424 are illustrated as being circular in shape, it will be understood that the apertures could have substantially any shape, including rectangular, square, oval, triangular, and the like (as discussed below). Additionally, while apertures 424 are illustrated as having generally uniform distributions within each of the distribution areas, the apertures could also have non-uniform distributions within one or more of the distribution areas. Furthermore, although distribution areas 426, 428, 430 are illustrated as being generally rectangular in shape, the distribution areas may have substantially any shape. For instance, the distribution areas may be circular, oval, rectangular, and the like. Moreover, while distribution areas 426, 428, 430 are illustrated as being generally discreet areas (e.g., each area has a particular aperture density), the distribution areas may be less discreet and more continuously changing (e.g., the aperture distribution density continuously decreases or increases away from the center of the return electrode). For instance, the distribution density of the apertures may gradually change within one or more of the distribution areas and/or across multiple distribution areas. By way of example, apertures may be formed in concentric rings, with each ring having an aperture density that is less dense than an aperture density of an adjacent internal ring.

In addition to functioning to enable the passage of magnetic, electric, or electromagnetic field lines (e.g., as part of an interrogation signal from a transponder detection unit), the apertures 424 in the conductive element can affect the capacitive coupling between the patient and the conductive element. Areas with fewer or less densely arranged apertures in the conductive element will allow for better capacitive coupling than areas with more or more densely arranged apertures. As a result, the different aperture distribution areas may provide for non-uniform current density features discussed in U.S. patent application Ser. No. 14/583,315.

Thus, for example, area 426 may provide sufficient capacitive coupling for a small patient (e.g., under 5 kg), while areas 228, 230 provide sufficient capacitive coupling for medium (e.g., between 5 kg to 15 kg) and large (e.g., above 15 kg) patients, respectively.

It will be appreciated that a return electrode similar to return electrode 420 may include fewer or more than three aperture distribution areas. Additionally, the different aperture distribution areas may be otherwise arranged relative to one another. For instance, aperture distribution area 426 may be arranged near an end and along at least a portion of the width of the return electrode. In other embodiments, two aperture distribution areas 426 may be included, one near a first end of the return electrode and the second near a second end of the return electrode. The various aperture distribution areas (e.g., in embodiments where more than one are included) may be visually identifiable via one or more visual indicators. For instances, each area may be color coded, labeled, or have area identifying indicia. The one or more visual indicators may identify the best position on the return electrode for a particular patient, such as based on the patient's weight.

Figure 6:
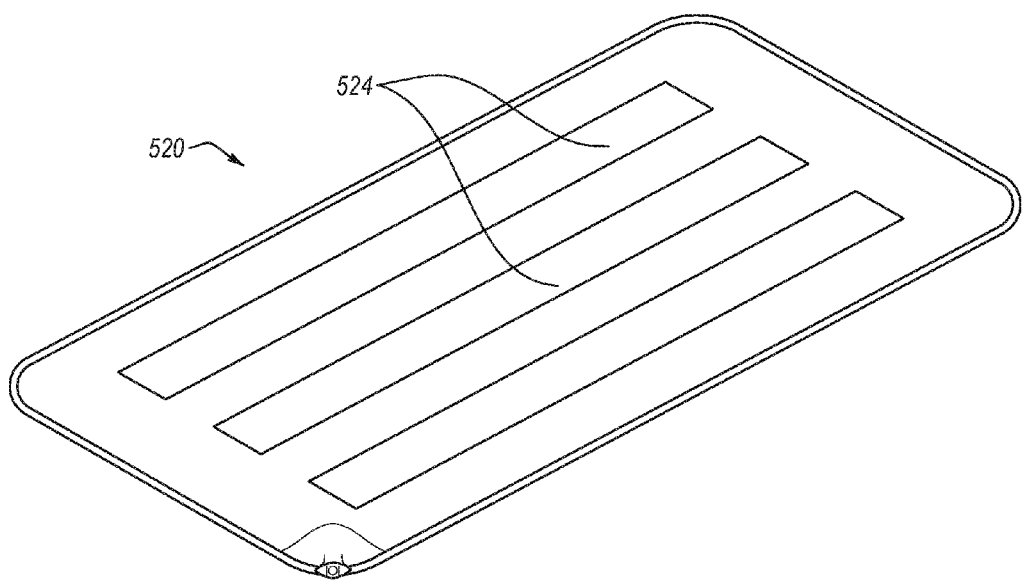
FIGS. 6-8 illustrate alternative embodiments of electrosurgical return electrodes having conductive elements with aperture arrays.
Figure 7:
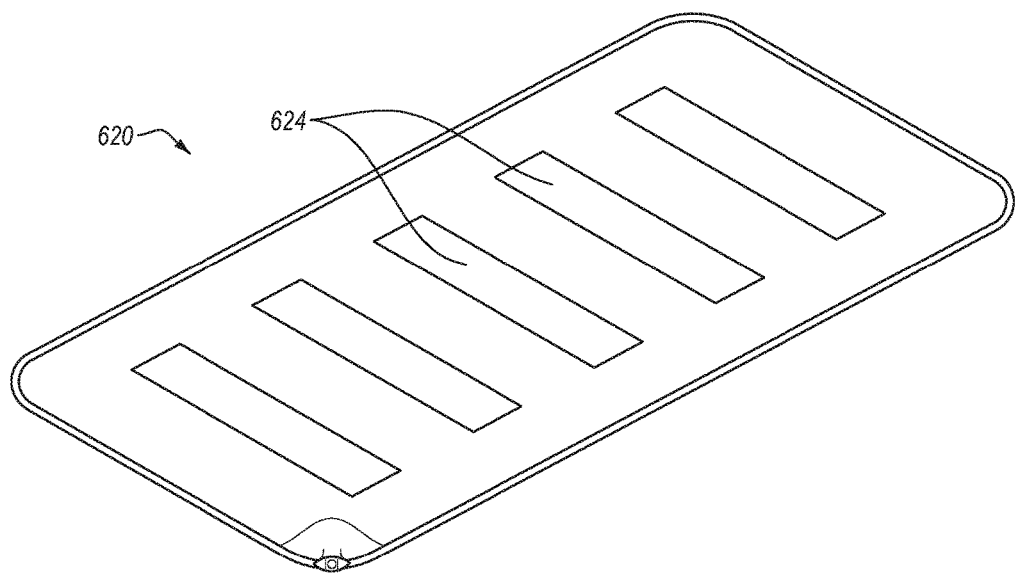

FIG. 6 illustrates another embodiment of a return electrode 520 having a conductive element with a plurality of apertures 524 configured to allow sufficient passage of a magnetic, electric, or electromagnetic field interrogation signal through the conductive element and the remainder of the return electrode 520. The embodiment illustrated in FIG. 6 may be similar to the embodiment illustrated in FIG. 5, and the description of the embodiment illustrated in FIG. 6 will therefore focus on the differences between the embodiments. As shown, the plurality of apertures 524 are formed as slits within the conductive element. In this embodiment, the slits are arranged so as to be parallel to a longitudinal axis of the return electrode 520. In other embodiments, slits may be arranged transverse to the longitudinal axis (e.g., perpendicular to the longitudinal axis or disposed at an angle of about 15, 30, 45, 60, or 75 degrees in either direction from the longitudinal axis). For example, the embodiment illustrated in FIG. 7 includes a plurality of apertures 624 formed as slits arranged perpendicular to the longitudinal axis of the return electrode 620.

One of skill in the art will recognize, in light of this disclosure, that in other embodiments, slits may be oriented non-uniformly on the conductive element. In some embodiments, a return electrode may not have a longitudinal axis (e.g., may have an overall square, circular, oval, or other symmetrical shape). In some embodiments, slats may be included and arranged at an angle relative to the longitudinal axis and/or one or more peripheral edges of the return electrode.

In the illustrated embodiment, the return electrode 520 includes 3 apertures (e.g., slits) distributed across the conductive element. Other embodiments include about 2 to 20, or about 3 to 10, or about 4 to 8 apertures.

As shown, the apertures may be distributed substantially uniformly across the surface area of the conductive element. Other embodiments may include areas having a greater or lesser density of apertures relative to other areas of the conductive element and/or areas having apertures of different size or shape. For example, some conductive element embodiments may have a lower amount of apertures at areas of the conductive element most often utilized as the effective surface area of the return electrode (i.e., the area used to make electrical contact with the patient and to receive current from the patient), and a higher density of apertures in areas less often utilized as the effective surface area, in order to ensure sufficient electrical contact for proper functioning of the return electrode while also allowing for sufficient passage of the magnetic, electric, or electromagnetic field signal through the conductive element (see FIG. 5, for example). In another example, the number of apertures may be increased at areas of the conductive element which more directly lay on top of the antennas of the transponder detection unit when the conductive element is affixed above or positioned above the detection unit.

Additionally, or alternatively, the configuration of one or more apertures may be different in certain areas of the conductive element. For example, some embodiments may include larger apertures (e.g., wider and/or longer slits, larger diameters) at areas less often used as the effective surface area of the return electrode to ensure passage of the magnetic, electric, or electromagnetic signal from an associated transponder detection unit, while including smaller apertures at areas more often used as the effective surface area of the return electrode in order to ensure sufficient electrical return from a patient in contact with the return electrode.

Figure 8:
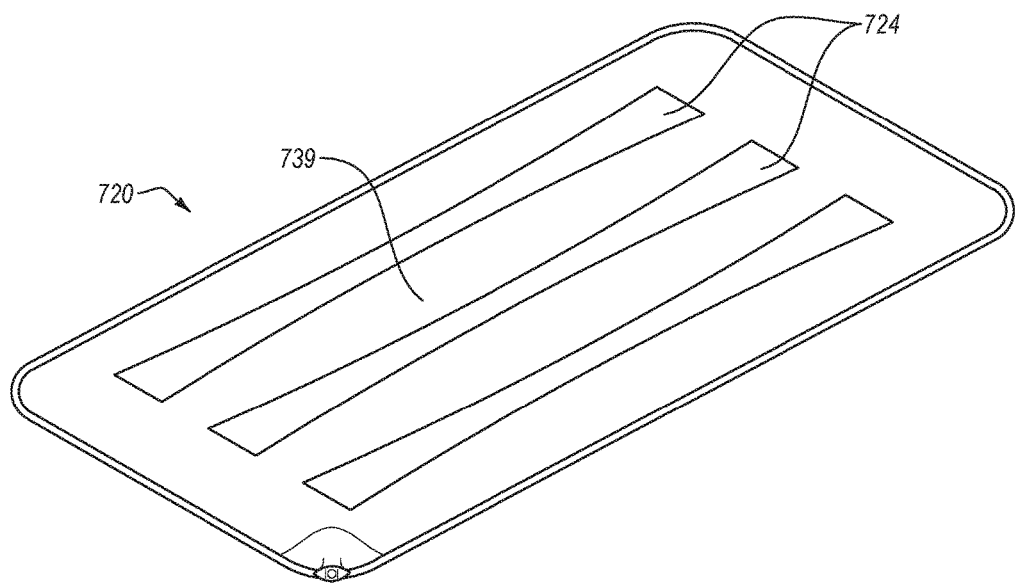

Similarly, one or more of the apertures themselves may be configured with smaller and larger relative sections. FIG. 8 illustrates one example of such an embodiment. As shown, the apertures 724 of the return electrode 720 have a tapered configuration such that they are narrower at an area 739 (e.g., near the center of the return electrode 720) and wider at more peripheral areas.

In some embodiments, the conductive element is configured such that about 10 to 90% of the surface area of the return electrode (e.g., the plan view surface area of one major surface, such as the top surface) is capable of conducting current from a patient positioned on the return electrode, while the remaining surface area is associated with an aperture or an aperture array for providing sufficient passage of the magnetic, electric, or electromagnetic signal from the associated transponder detection unit. In other embodiments, about 20, 30, 40, 50, 60, 70, or 80%, or ranges between any two of such values, of the surface area of the return electrode is capable of conducting current from a patient positioned on the return electrode, while the remaining surface area is associated with apertures for providing sufficient passage of the magnetic, electric, or electromagnetic signal from the associated transponder detection unit.

Figure 9:
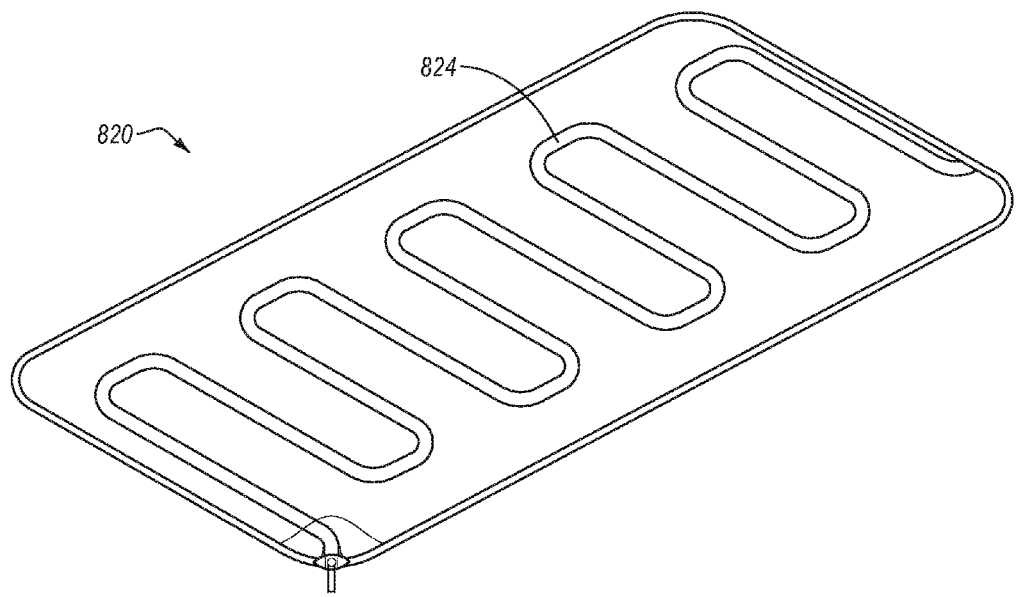
FIG. 9 illustrates an embodiment of an electrosurgical return electrode having a conductive trace.

FIG. 9 illustrates another embodiment of a return electrode 820 configured for operation with an associated transponder detection unit. In this embodiment, the conductive element is formed, at least in part, from a trace 824 of conductive material. The trace 824 can be applied to a magnetic, electric, or electromagnetic field transparent sheet (e.g., a flexible polymer-based sheet and/or a section of fabric material) which is incorporated into the return electrode 820. The trace 824 is applied so as to provide sufficient conduction from a patient to enable the return electrode 820 to function during an electrosurgical procedure, while also leaving a sufficient amount of surface area for providing transparency to a magnetic, electric, or electromagnetic signal from an associated transponder detection unit.

Figure 10:
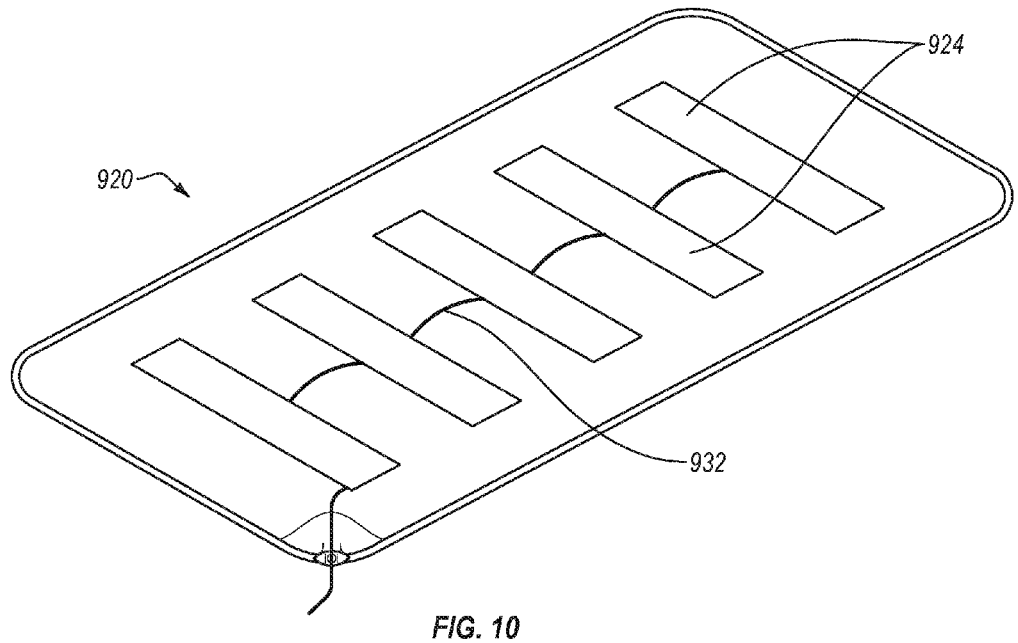
FIG. 10 illustrates an embodiment of an electrosurgical return electrode having a conductive element formed as a plurality of electrically connected panels.

FIG. 10 illustrates another embodiment of a return electrode 920 having a conductive element formed from a plurality of interconnected panels 924. The panels may be connected by one or more connectors 932. As shown, the connectors 932 may be formed as thin strips or wires configured to provide electrical communication between separate panels within the return electrode 920 without taking up much surface area. The panels 924 are arranged to leave sufficient gaps between adjacent panels to provide sufficient magnetic, electric, or electromagnetic transparency to the return electrode 924. The conductive element may be configured to provide gaps between adjacent panels ranging from about 0.25 to 18 inches, or about 0.5 to 12 inches, or about 1 to 6 inches, or about 1 to 3 inches.

Figure 11A:
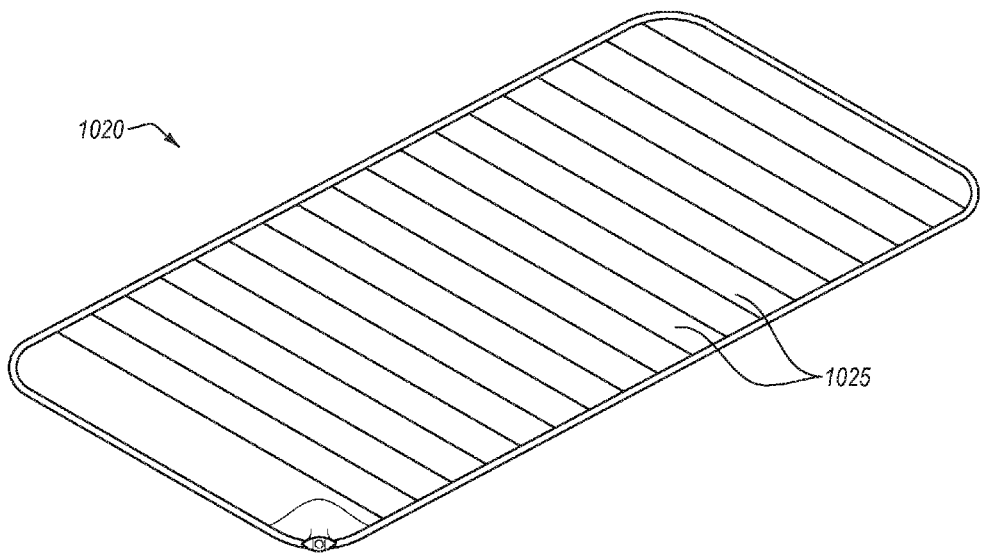
FIGS. 11A and 11B illustrate an embodiment of an electrosurgical return electrode having an adjustable aperture array.
Figure 11B:
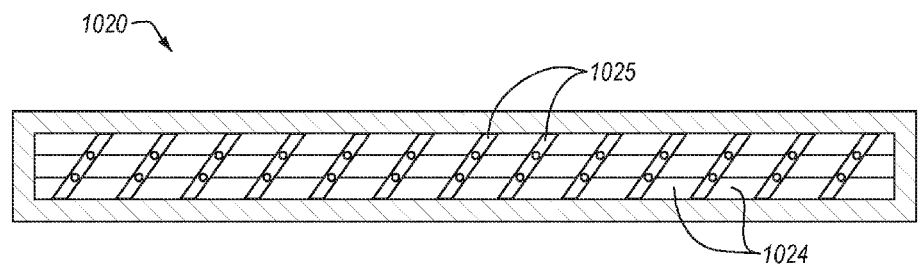

FIGS. 11A and 11B illustrate another embodiment of a return electrode 1020 configured to provide adjustable magnetic transparency. The illustrated embodiment includes a conductive element formed as a plurality of adjustable slats 1025. In the configuration illustrated in FIG. 11A (i.e., a closed configuration), the adjustable slats 1025 are oriented so as to cover most or all of the plan-view surface area of the return electrode 1020. The slats 1025 are configured to be moveable from the closed configuration of FIG. 11A to an open configuration illustrated in cross-section in FIG. 11B. As shown in FIG. 11B, the slats 1025 are rotated to provide a plurality of gaps 1024 between the slats 1025. Positioning the slats 1025 in this configuration may provide sufficient passage of magnetic, electric, or electromagnetic field lines from an associated transponder detection unit. As shown by this embodiment, the adjustable conductive element may be formed as a plurality of slats configured to rotate in a blind-like fashion.

In preferred embodiments, the adjustable components of the conductive element are configured to be adjustable without the need to move or reposition a patient placed upon the return electrode. Using the embodiment of FIGS. 11A and 11B as an example, the return electrode may be configured with adequate clearance and structural features surrounding the conductive element to allow movement of the slats 1024 from the closed toward the open configuration and vice versa. In addition, or alternatively, the conductive element may be formed from a material that is sufficiently flexible to allow desired positional adjustments and reorientation even when subjected to pressure applied because of a patient positioned on the return electrode.

Although the embodiment illustrated in FIGS. 11A and 11B shows the plurality of slats 1025 oriented transverse to the longitudinal axis of the return electrode 1020, one of skill in the art will recognize, in light of this disclosure, that in other embodiments, such slats may be oriented parallel to the longitudinal axis of the return electrode. In other embodiments, a return electrode may not have a longitudinal axis (e.g., may have an overall square, circular, oval, or other symmetrical shape). In some embodiments, slats may be included and arranged at an angle relative to the longitudinal axis and/or one or more peripheral edges of the return electrode.

Embodiments configured with adjustable features for enabling adjustment of the magnetic, electric, and electromagnetic transparency of the return electrode, such as those shown in FIGS. 11A and 11B, can beneficially allow a greater surface area contact of the conductive element with a patient during an electrosurgical procedure. After the electrosurgical procedure is complete, and/or at points during the procedure when it is desired to check for the presence of one or more transponders, the conductive element and/or other return electrode components may be adjusted to increase the magnetic, electric, or electromagnetic transparency of the return electrode and provide sufficient passage of an interrogation signal from an underlying transponder detection unit. Using the embodiment of FIGS. 11A and 11B as an example, the slats 1025 may be moved from the closed configuration shown in FIG. 11A toward the open position shown in FIG. 11B. One of skill in the art will understand, in light of this disclosure, that it may not be necessary in all instances to fully open the slats 1025 in order to provide sufficient magnetic, electric, or electromagnetic transparency to the return electrode 1020, and that it may not be necessary in all instances to fully close the slats 1025 to provide sufficient capacitive contact with a patient positioned on the return electrode 1020.

Figure 12A:
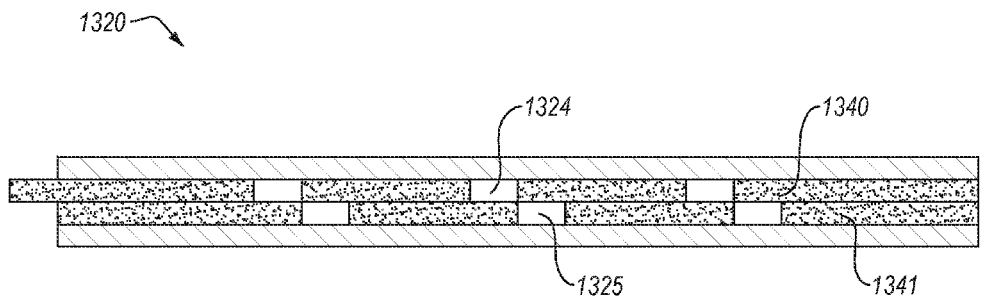
FIGS. 12A and 12B illustrate another embodiment of an electrosurgical electrode having an adjustable aperture array.
Figure 12B:
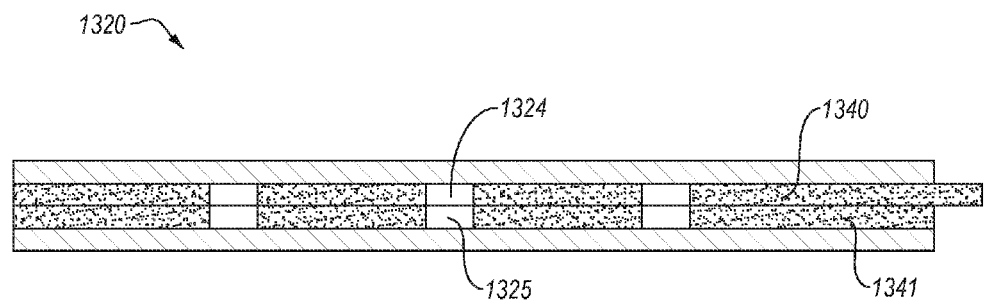

Other embodiments include other features and/or components for enabling adjustable magnetic, electric, or electromagnetic transparency to the return electrode. For example, some embodiments may include a conductive element having at least a portion that is repositionable with respect to other portions of the return electrode in order to adjust the number and/or size of gaps for the passage of a magnetic, electric, or electromagnetic interrogation signal. FIGS. 12A and 12B illustrate cross-sectional views of an embodiment of a return electrode 1320 having a conductive element formed from two separate sections 1340, 1341 adjustable to enable the return electrode 1320 to be alternated between a closed configuration (FIG. 12A) and an open configuration (FIG. 12B). Although two sections 1340, 1341 are shown, other embodiments include more than two of such sections. In some embodiments, one piece may be adjusted relative to the other piece (e.g., by pulling a tab that is joined to the adjustable piece and that extends to the exterior of the return electrode) to adjust the size or amount of open gaps extending through the conductive element.

In the illustrated embodiment, an upper section 1340 of the conductive element having one or more apertures 1324 is positioned above a lower section 1341 of the conductive element having one or more apertures 1325. The upper and lower sections 1340, 1341 are configured such that in a closed configuration the apertures 1324, 1325 of the upper and lower sections are substantially misaligned. In this position, the number and size of gaps extending through the conductive element is decreased or eliminated, while the surface area available for conductive contact with a patient is increased. The upper and/or lower sections 1340, 1341 are configured to be moveable, such that the corresponding upper and lower apertures 1324, 1325 can be moved toward alignment (e.g., by sliding one of the sections relative to the other). The greater alignment between the corresponding apertures enables greater magnetic, electric, or electromagnetic transparency to the return electrode.

As used herein, the terms "open configuration" and "closed configuration" and their synonyms, do not require that the conductive element be made completely magnetically, electrically, or electromagnetically transparent or completely magnetically, electrically, or electromagnetically opaque, respectively. Rather, unless specified otherwise, the terms represent relative levels of aperture openness and associated magnetic, electric, or electromagnetic transparency. For example, an open configuration may still include some level of interaction between a magnetic, electric, or electromagnetic interrogation signal and the conductive element, although at levels insufficient to cause inoperability of an associated transponder detection unit. Likewise, a closed configuration may still allow passage of a magnetic, electric, or electromagnetic interrogation signal, and may even allow sufficient passage to allow effective transponder detection. However, a greater surface area for contact with a patient is made available in the closed configuration relative to the open configuration. In addition, one of skill in the art will recognize, in light of this disclosure, that various levels or gradations of openness are made possible by at least some of the embodiments described herein.

Figure 13:
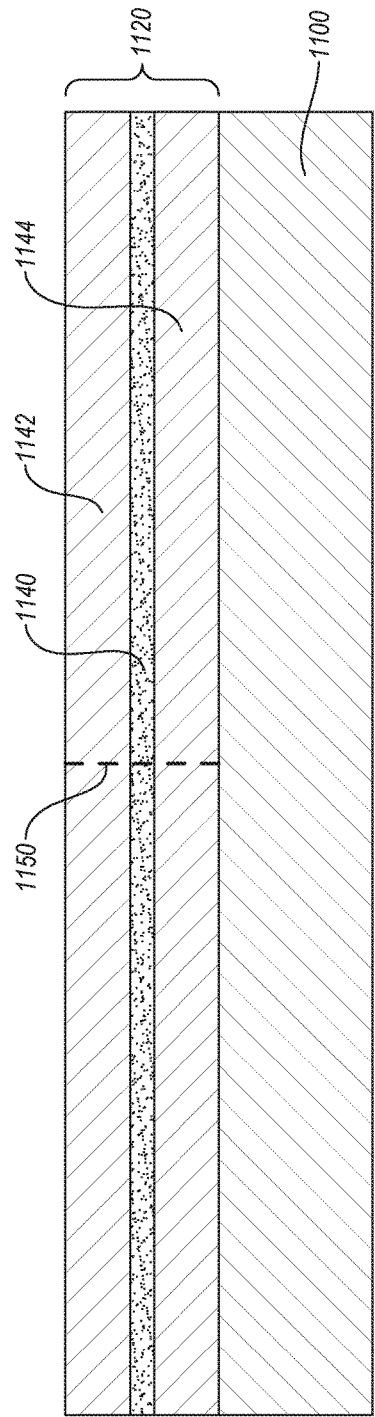
FIGS. 13 and 14 illustrate embodiments of electrosurgical return electrode and transponder detection systems.

FIG. 13 illustrates an example cross-sectional view of an embodiment of an integrated wireless transponder detection and return electrode system, including a transponder detection unit 1100 associated with a return electrode unit 1120. As indicated above, such embodiments may be formed as "one-piece" pads or mats, having a transponder detection unit 1100 that is joined to the return electrode unit 1120. Alternatively, the transponder detection unit 1100 and return electrode unit 1120 may be formed as separate pieces that are positionable in an operable relationship by stacking the return electrode unit 1120 at least partially on top of the transponder detection unit 1100, as illustrated. In some embodiments, one or both of pads 1142, 1144 are omitted. In particular, pad 1144 may be omitted in embodiments in which the transponder detection unit 1100 already includes one or more pad or pad-like layers (e.g., gel, foam, etc.).

The transponder detection unit 1100 may be configured as the detection unit described in connection with FIGS. 1 and 2. Alternatively, one or more other transponder detectors known in the art may be included. In some embodiments, the transponder detection unit 1100 will be configured with a mat or pad-like construction to enable detection of transponders within an area above the return electrode unit 1120 without the need for an additional interrogation signal transmitter and without the need of adjusting or repositioning a patient within the targeted interrogation signal range.

In the illustrated embodiment, the return electrode unit 1120 includes an area 1150 of weakened integrity (e.g., a perforated area). The area 1150 is configured to provide a break-away or separation point in the return electrode unit 1120, such that when transponder detection functionality is desired, or when insufficient levels of a magnetic, electric, or electromagnetic interrogation signal are able to pass through the return electrode unit 1120, the return electrode unit 1120 may be pulled apart to form one or more gaps for improved transmission of the magnetic, electric, or electromagnetic signal through the return electrode unit 1120. The illustrated embodiment shows the area 1150 extending completely through the return electrode unit 1120. In other embodiments, an area of weakened integrity may only extend through the conductive element 1140, or through the conductive element and only a portion of the remaining thickness of the return electrode. Such embodiments allow the conductive element to be pulled apart to reveal or to enlarge magnetically, electrically, or electromagnetically transparent gaps in the device, while allowing the integrity of other portions of the return electrode (e.g., pad 1142 and/or pad 1144) to be maintained. Other embodiments may omit any areas of intentionally weakened integrity.

In some embodiments, one or more components of the integrated wireless transponder detection and return electrode system are configured to enable adjustment of the thickness of the return electrode unit 1120, or to otherwise provide for adjustment to the distance between the transponder detection unit 1100 and the conductive element 1140. Increasing the distance between the antenna(s) or other transmitting elements of the transponder detection unit 1100 and the conductive element 1140 has been found to increase the ability of a magnetic, electric, or electromagnetic interrogation signal to reach targeted areas above the return electrode unit 1120. In one embodiment, the return electrode component 1120 includes an inflatable section that can move the conductive element 1140 further away from the detection unit 1100 upon inflation. For example, pad 1144 may be inflatable or may include one or more inflatable components. Additionally, or alternatively, one or more inflatable components may replace pad 1144 or may be positioned adjacent to pad 1144. The introduction of air or other fluid into the one or more inflatable components thereby increases the thickness of the area between the conductive element 1140 and the detection unit 1100, enabling more effective use of the detection unit 1100.

Such embodiments may beneficially allow performance of an electrosurgical procedure while the return electrode unit 1100 is in a thin or deflated configuration. After the procedure is completed, or at a time during the procedure when transponder detection is desired, the return electrode component 1120 may be moved to a thick or inflated configuration in order to enable or augment transponder detection. The return electrode unit 1120 may be adjusted to different levels at or between the thick/inflated and thin/deflated configurations according to a user's needs and preferences.

Other embodiments utilize other components to achieve the same functionality. For example, some embodiments may include one or more springs, levers, jacks, height-adjustable platforms, or other means for adjusting the distance between the detection unit 1100 and the conductive element 1140.

Figure 14:
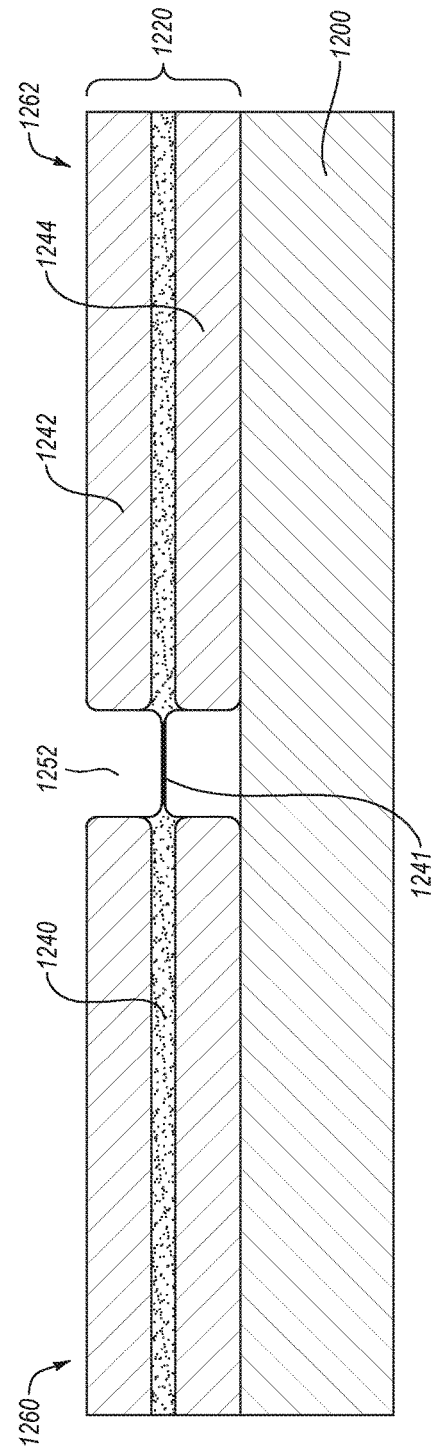

FIG. 14 illustrates another cross-sectional view of an embodiment of an integrated wireless transponder detection and return electrode system, including a transponder detection unit 1200 associated with a return electrode unit 1220. In the illustrated embodiment, transponder detection unit 1200 is associated with return electrode unit 1220. In this embodiment, the return electrode unit 1220 is formed as a plurality of modular sections, including modular section 1260 and modular section 1262. In this embodiment, the return electrode unit 1220 includes separate and electrically joinable pieces (e.g., sections 1260, 1262) that are independently positionable upon the transponder detection unit 1200. The modular sections 1260, 1262 may be positioned on the transponder detection unit 1200 so as to leave one or more gaps 1252 between sections to allow for passage of a magnetic, electric, or electromagnetic interrogation signal. As shown, the modular sections 1260, 1262 may be connected by a section 1241. In this embodiment, the section 1241 is a relatively small wire section of the conductive element 1240 extending between the separate modular sections 1260, 1262 to provide electrical communication between the sections 1260, 1262. In some embodiments, the section 1241 is a thin wire or strip or otherwise has a small plan-view surface area in order to minimize interaction or interference with the passage of a magnetic, electric, or electromagnetic signal through the associated gap 1252. The size of the one or more gaps 1252 between adjacent sections may range from about 0.25 to 18 inches, or about 0.5 to 12 inches, or about 1 to 6 inches, or about 1 to 3 inches.

Referring now to the disclosure generally, some embodiments may include components that enable the electrical current to be passed to the conductive element in order to increase the magnetic, electric, or electromagnetic transparency of the conductive element. For example, some embodiments may involve components (e.g., power supply, ammeter, etc.) configured to pass current to the conductive element in order to prevent the conductive element from carrying a charge. In one example, current is passed to the conductive element sufficient to counteract any induced current caused by the interaction of a magnetic, electric, or electromagnetic interrogation signal directed passed, through, or nearby the conductive element. Similarly, in some embodiments, a conductive element is at least partially formed from a material that has sufficient magnetic, electric, or electromagnetic transparency but is capable of conducting electricity.

In some embodiments, at least a portion of the conductive element and/or other portions of the return electrode are formed from a carbon-based or carbon-coated material, such as a, carbon fiber, carbon fabric, or carbon-coated fabric. In some embodiments, at least a portion of the conductive element and/or other portions of the return electrode are formed from a carbon nanotube coated material. In some embodiments, at least a portion of the conductive element and/or other portions of the return electrode are formed from a graphene based or coated material.

In some embodiments, at least a portion of the conductive element and/or other portions of the return electrode are formed from a polarized material configured to allow passage of types or wavelengths of fields while blocking or conducting other types or wavelengths.

The embodiments illustrated herein are examples only, and one of skill in the art will recognize, in light of this disclosure, that various other embodiments are included within the disclosure. For example, some embodiments may include conductive elements having apertures of various sizes and/or shapes, and the apertures may be uniform or non-uniform in size, shape, orientation, adjustability, etc. Features and/or components of a given embodiment may be combined with or replaced by features and/or components of a separate embodiment.

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical return electrode comprising:
   a conductive element configured to conduct electrical current, the conductive element having opposing first and second major surfaces and including an aperture array configured to allow passage of a magnetic, electric, or electromagnetic interrogation signal from an associated transponder detection unit through the conductive element, and
   a patient contact pad positioned adjacent the first major surface of the conductive element and configured to be disposed between the conductive element and a patient when the patient is at least partially positioned upon the patient contact pad;
   wherein the electrosurgical return electrode is configured to be at least partly positionable upon the transponder detection unit with the second major surface facing the transponder detection unit, and
   wherein the aperture array is configured to be adjustable between an open configuration and a closed configuration to thereby adjust the magnetic, electric, or electromagnetic transparency of the electrosurgical return electrode.

2. An electrosurgical return electrode according to claim 1, wherein the conductive element is formed as a plurality of substantially parallel rotatable slats, a plurality of apertures being disposed therebetween in the open configuration, the slats being configured to rotate to adjust the apertures between the open configuration and the closed configuration.

3. An electrosurgical return electrode according to claim 2, wherein the apertures are substantially covered by overlapping or adjacent edges of the slats in the closed configuration.

4. An electrosurgical return electrode according to claim 3, wherein the conductive element includes an upper section having one or more upper apertures and a lower section having one or more lower apertures, the upper apertures and lower apertures being in greater alignment in the open configuration than in the closed configuration.

5. An electrosurgical return electrode according to claim 4, at least one of the upper or lower sections being slidably adjustable relative to the other section.

6. An electrosurgical return electrode kit according to claim 1, further comprising an area of weakened integrity configured to enable at least a portion of the return electrode to be broken away from the remainder of the return electrode.

7. An electrosurgical return electrode kit according to claim 1, wherein the return electrode is formed from a plurality of electrically connected modular sections, the aperture array being defined at least in part by gaps formed between the plurality of modular sections.

8. An electrosurgical return electrode kit according to claim 7, wherein the modular sections are electrically connected by one or more wires or strips of conductive material.

9. An electrosurgical return electrode kit according to claim 1, further comprising a height-adjustable component configured to adjust the thickness of at least a portion of the return electrode to enable movement of the conductive element further away from an associated transponder detection unit when the return electrode is positioned upon the transponder detection unit.

10. An electrosurgical return electrode and transponder detection system, comprising:
   a transponder detection unit comprising one or more antennae; and
   an electrosurgical return electrode positioned above the transponder detection unit, the electrosurgical electrode comprising:
      a conductive element configured to conduct electrosurgical current and return the electrosurgical current back to a an electrosurgical generator, the conductive element having opposing first and second major surfaces and including an aperture array configured to allow passage of a magnetic, electric, or electromagnetic interrogation signal from the transponder detection unit through the conductive element, the aperture array is sized and positioned in relation to at least one of the one or more antennae such that the interrogation signal is caused to be above a threshold strength, and wherein a surface area of the first major surface and a size of the aperture array cooperate to both maintain at least a selected amount of conductivity for the conductive element and enable the interrogation signal to be above the threshold strength, wherein the aperture array is configured to be adjustable between an open configuration and a closed configuration to thereby adjust the magnetic, electric, or electromagnetic transparency of the electrosurgical return electrode;
   wherein the transponder detection unit and electrosurgical return electrode are operably associated such that the transponder detection unit is adapted to detect a transponder located in a target area above the electrosurgical return electrode and within range of the transponder detection unit.

11. An electrosurgical return electrode and transponder detection system according to claim 10, wherein the system is configured to enable detection of the transponder when a patient is positioned upon the return electrode unit without repositioning the patient relative to the return electrode unit.

12. An electrosurgical return electrode and transponder system according to claim 10, wherein the return electrode unit and the transponder detection unit are at least partially affixed to form an integrated one-piece structure.

13. An electrosurgical return electrode and transponder detection system according to claim 12, wherein the one-piece structure is a mat or pad.

14. An electrosurgical return electrode and transponder detection system according to claim 10, wherein the transponder detection unit is configured to transmit a magnetic, electric, or electromagnetic interrogation signal, and wherein the electrosurgical return electrode is configured to provide sufficient passage of the magnetic, electric, or electromagnetic interrogation signal through the electrosurgical return electrode to the transponder located above the electrosurgical return electrode.

15. A method for detecting a transponder in an electrosurgical environment, the method comprising:
   positioning a patient at least partially upon an electrosurgical return electrode and transponder detection system according to any one of claims 10 to 14;
   actuating the transponder detection unit to send a magnetic, electric, or electromagnetic interrogation signal to a target area that includes or is near at least a portion of the patient; and
   receiving a return signal from a transponder indicating presence of the transponder at the target area.

16. An electrosurgical return electrode and transponder detection unit kit, the kit comprising:
   a transponder detection unit comprising one or more antennae; and
   an electrosurgical return electrode comprising:
      a conductive element configured to conduct electrosurgical current and return the electrosurgical current back to a an electrosurgical generator, the conductive element having opposing first and second major surfaces and including an aperture array configured to allow passage of a magnetic, electric, or electromagnetic interrogation signal from the transponder detection unit through the conductive element, wherein a surface area of the first major surface and a size of the aperture array cooperate to both maintain at least a selected amount of conductivity for the conductive element and enable the interrogation signal to be above a threshold strength; and
      a patient contact pad positioned adjacent the first major surface of the conductive element and configured to be disposed between the conductive element and a patient when the patient is at least partially positioned upon the patient contact pad, the patient contact pad being formed of a non-conductive or dielectric material;
   wherein the electrosurgical return electrode is configured to be at least partly positionable upon the transponder detection unit with the second major surface facing the transponder detection unit; and
   wherein the aperture array is configured to be adjustable between an open configuration and a closed configuration to thereby adjust the magnetic, electric, or electromagnetic transparency of the electrosurgical return electrode.

17. A kit according to claim 16, wherein the transponder detection unit comprises a transponder detection unit pad positioned adjacent the second major surface of the conductive element and configured to be disposed between the conductive element and the transponder detection unit when the electrosurgical return electrode is at least partially positioned upon the transponder detection unit.

18. A kit according to claim 16, wherein the aperture array includes a plurality of apertures.

19. A kit according to claim 18, wherein the aperture array includes 2 to 20, or 3 to 10, or 4 to 8 apertures.

20. A kit according to claim 18, wherein the aperture array includes a plurality of distribution areas having separate aperture configurations.

21. A kit according to claim 20, wherein the separate aperture configurations include separate aperture densities.

22. A kit according to claim 21, wherein a second distribution area included among the plurality of distribution areas is disposed peripherally around at least a portion of a first distribution area included among the plurality of distribution areas, and wherein the second distribution area includes a higher aperture density than the first distribution area.

23. A kit according to claim 20, wherein the separate aperture configurations include separate aperture sizes.

24. A kit according to claim 23, wherein a first distribution area included among the plurality of distribution areas includes apertures having a smaller average size than apertures of a second distribution area included among the plurality of distribution areas, the second distribution area being disposed peripherally around at least a portion of a first distribution area.

25. A kit according to claim 20, wherein the separate aperture configurations include separate aperture shapes.

26. A kit according to claim 25, wherein at least one of the apertures extends across at least a portion of a first distribution area and at least a portion of a second distribution area, and has a smaller size within a first distribution area and a larger size within a second distribution area, the second distribution area being disposed peripherally around at least a portion of a first distribution area.

27. A kit according to claim 16, wherein the aperture array includes circular or ovoid shaped apertures.

28. A kit according to claim 16, wherein the conductive element is formed as a plurality of electrically connected panels, the aperture array being defined by gaps between the plurality of panels.

29. A kit according to claim 16, wherein the aperture array includes slits.

30. A kit according to claim 29, wherein the slits are substantially aligned with a longitudinal axis of the electrosurgical return electrode.

31. A kit according to claim 29, wherein the slits are oriented transverse to a longitudinal axis of the electrosurgical return electrode.

32. A kit according to claim 16, wherein the aperture array covers 10 to 90% of the plan view surface area of the conductive element.

* * * * *